United States Patent [19]
Iseberg et al.

[11] Patent Number: 6,056,698
[45] Date of Patent: May 2, 2000

[54] APPARATUS FOR AUDIBLY MONITORING THE CONDITION IN AN EAR, AND METHOD OF OPERATION THEREOF

[75] Inventors: Steven J. Iseberg, Rolling Meadows; Mead C. Killion, Elk Grove Village, both of Ill.; Greg R. Shaw, Calgary, Canada

[73] Assignee: Etymotic Research, Inc., Elk Grove Village, Ill.

[21] Appl. No.: 08/971,520

[22] Filed: Nov. 17, 1997

Related U.S. Application Data

[63] Continuation-in-part of application No. 08/832,277, Apr. 3, 1997.

[51] Int. Cl.[7] ...................................................... A61B 5/00
[52] U.S. Cl. ........................................... 600/558; 600/559
[58] Field of Search ..................................... 128/864–686; 600/558, 559, 600

[56] References Cited

U.S. PATENT DOCUMENTS

| | | | |
|---|---|---|---|
| 4,024,499 | 5/1977 | Bosscher | 600/559 |
| 4,321,427 | 3/1982 | Singh | 600/559 |
| 4,601,295 | 7/1986 | Teele | 600/559 |
| 4,879,749 | 11/1989 | Levitt | 73/585 |

*Primary Examiner*—Michael A. Brown
*Attorney, Agent, or Firm*—McAndrews, Held & Malloy, Ltd.

[57] ABSTRACT

The present invention relates generally to devices that monitor the condition within an ear, and more specifically to devices that are external to the ear and monitor the condition within the ear using a probe placed within the ear canal. The device comprises a signal generator for forming an electrical signal based on a condition within an ear, and an output for making the electrical signal accessible to an audio transducer. For example, in DPOAE testing, the signal generator is a microphone that forms an electrical signal from any otoacoustic emissions within the ear, any test signal within the ear, and any noise within the ear; and the output is an earphone jack for making the electrical signal accessible to an earphone worn by the operator. Thus, the operator can monitor any extraneous noise within the ear canal and monitor the progress of the test while the test is being performed.

21 Claims, 3 Drawing Sheets

APPARATUS FOR AUDIBLY MONITORING THE CONDITION IN AN EAR, AND METHOD OF OPERATION THEREOF

CROSS-REFERENCE TO RELATED APPLICATIONS

This is a continuation-in-part of application Ser. No. 08/832,277, filed on Apr. 3, 1997, now pending, which is incorporated by reference.

STATEMENT REGARDING FEDERALLY SPONSORED RESEARCH OR DEVELOPMENT

Not Applicable

BACKGROUND OF THE INVENTION

The present invention relates generally to devices that monitor the condition within an ear, and more specifically to devices that are external to the ear and monitor the condition within the ear using a probe placed within the ear canal. Even more specifically, the present invention relates to a hearing tester which emits test signals into the ear through a probe placed within the ear canal, and then uses the distortion-product otoacoustic emissions (DPOAE) from the ear to determine middle-ear function.

Devices that monitor the condition within an ear use a probe placed within the ear canal. The probe is placed within the ear canal by the person performing the test (the "operator"). For example, in DPOAE testing, all existing equipment uses a probe which seals into the ear canal. The probe is either attached to the device through a cable or, as illustrated in patent application Ser. No. 08/832,277, the probe is integrated into a hand-held device. In addition, existing devices display the results of the test on a screen while the test is being performed. The screen is external to the device.

One problem with existing devices is their susceptibility to extraneous noise introduced into the ear canal or measurement system. For example, in DPOAE testing, the otoacoustic emissions produced by a healthy ear are extremely small in magnitude. The emissions typically range from −10 dB SPL (Sound Pressure Level) to +20 dB SPL. Any kind of extraneous noise introduced into the ear canal or measurement system can mask these emissions and give a false negative response.

Sources of extraneous noise are external noise from the environment and biological noise from within the person whose ear is being tested. Environmental noise arises from improper positioning of the test probe within the ear canal, thus allowing noise to enter the ear canal from the sides of the test probe. Biological noise arises from teeth grinding, sneezing, etc. on the part of the person whose ear is being tested.

Thus, when using existing devices, there is a need to determine if extraneous noise is present, to determine the source of the noise, and to eliminate the noise before and during a test. For example, when using the hand-held device of patent application Ser. No. 08/832,277, there is a need to know if environmental noise is present so that the operator can eliminate the environmental noise by repositioning the hand-held device against the patient's ear and applying the appropriate amount of pressure to maintain a seal between the test probe and the entrance to the ear canal.

Another problem with existing devices is the use of an external display. The operator monitors the progress of the test while the test is being performed by viewing the display. Simultaneously performing the test and monitoring the display can be awkward, especially when the operator is concentrating on the proper placement of the test probe within the ear canal. For example, in the hand-held device illustrated in patent application Ser. No. 08/832,277, holding the device so that the test probe is properly positioned within the ear, and simultaneously viewing the display can be difficult. Thus, a need exists for using the device without the necessity of monitoring the display, or in other words, "eyes-free" operation.

BRIEF SUMMARY OF THE INVENTION

Accordingly, one object of the invention is an ear monitoring device which can provide an operator with an indication of the extraneous noise within the ear canal while the operator is performing the test.

Another object of the invention is an ear monitoring device which can provide the operator with an indication of the progress of the test without requiring the operator to monitor the display.

These and other objects of the invention will become apparent from the present drawings and specification.

These and other objects and advantages are provided in an improved apparatus for monitoring the condition in an ear which is different from prior art devices in that there is provided a device having a signal generator for forming an electrical signal based on a condition within an ear, and an output for making the electrical signal accessible to an audio transducer external to the apparatus. For example, in DPOAE testing, the signal generator is a microphone that forms an electrical signal from any otoacoustic emissions within the ear, any test signal within the ear, and any noise within the ear; and the output is an earphone jack for making the electrical signal accessible to an earphone worn by the operator. Thus, the operator can monitor any extraneous noise and the progress of the test while the test is being performed.

In addition, these and other objects and advantages are provided in an improved method for monitoring the condition in an ear which is different from prior art methods in that there is provided a method which performs the steps of forming an electrical signal based on the condition within an ear, and making the electrical signal accessible to an external audio transceiver.

DETAILED DESCRIPTION OF THE INVENTION

While the invention will be described in connection with one or more embodiments, it will be understood that the invention is not limited to those embodiments. On the contrary, the invention includes all alternatives, modifications, and equivalents as may be included within the spirit and scope of the appended claims.

Figure 1:
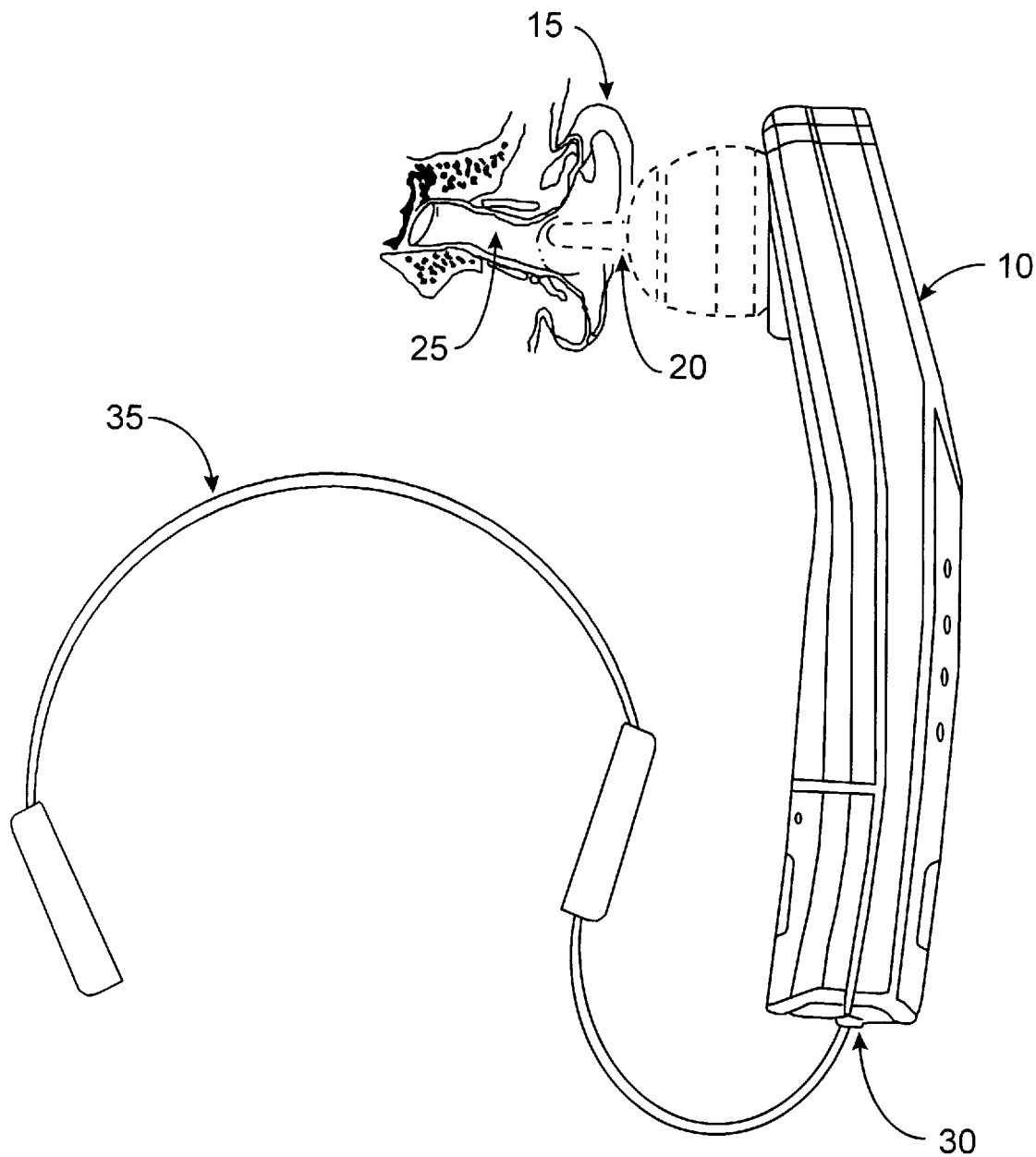
FIG. 1 is an overview diagram showing the environment in which an ear monitoring device is used in accordance with the present invention.

FIG. 1 is an overview diagram showing the environment in which an ear monitoring device is used in accordance with the present invention. An ear monitoring device 10 is illustrated. A patient's ear 15 is also illustrated. A probe 20 is connected to the ear monitoring device 10. The probe 20 is positioned within an ear canal 25 of the patient's ear 15. The ear monitoring device 10 is shown as a device which is held up to the patient's ear 15, and the probe 20 is integrated with the ear monitoring device 10. However, the ear monitoring device 10 may also be remote from the ear 15 and connected to the probe 20 through a cable. The ear monitoring device has an output 30 for making the conditions within the ear canal 25 available to an audio transducer 35. The audio transducer 35 is shown as a set of earphones. However, the audio transducer 35 may be any type of transducer that converts electrical signals to sound, such as a speaker. Also, the output 30 is shown as an output jack. However, the output 30 may be a hard-wired connection of the audio transducer 35 to the ear monitoring device 10, or any type of electrical connection.

Figure 2:
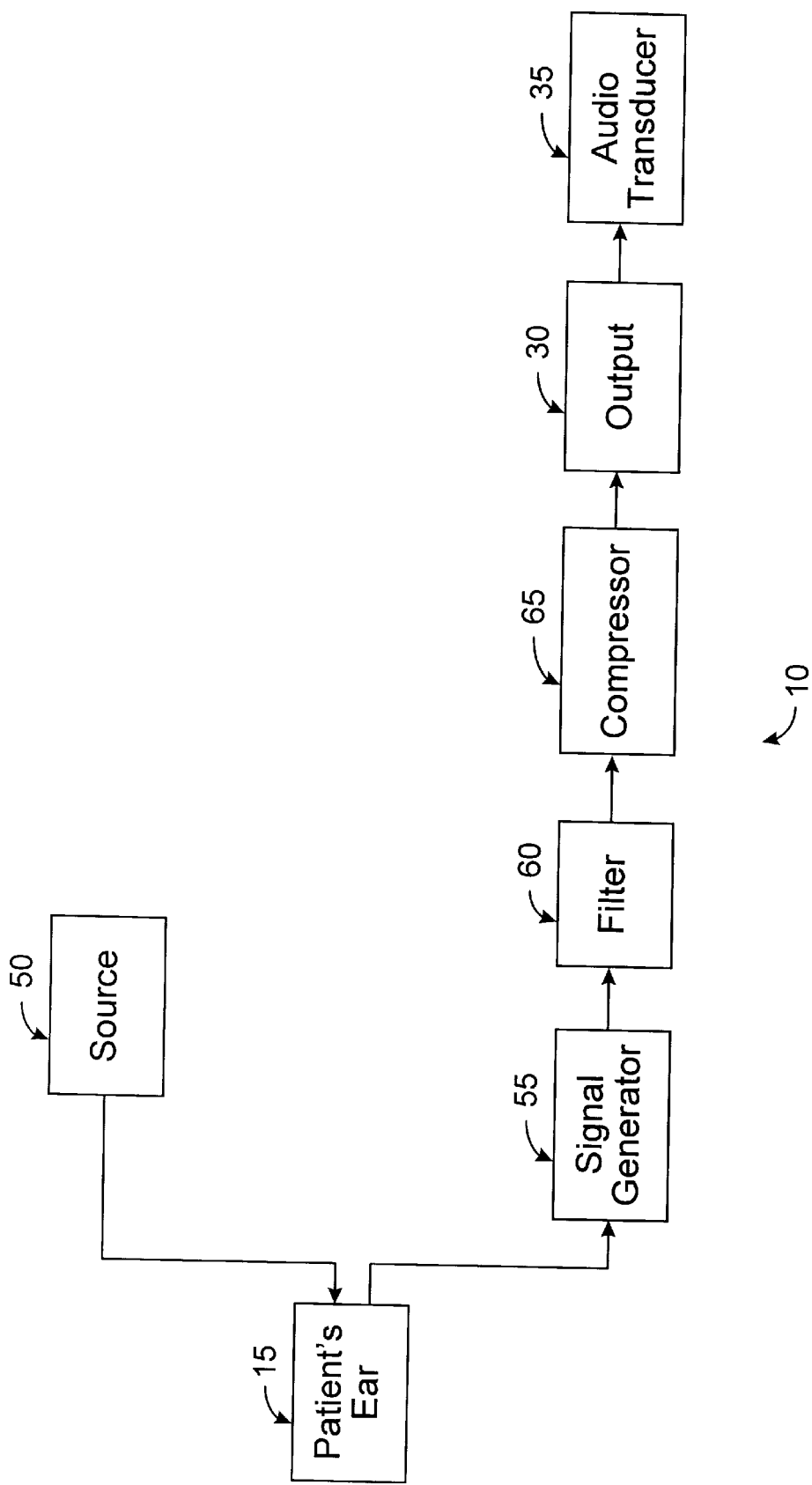
FIG. 2 is a block diagram of an ear monitoring device according to the present invention.

FIG. 2 is a block diagram of an ear monitoring device according to the present invention. The block diagram shows one embodiment of the ear monitoring device 10, but as will be discussed later, other embodiments exist which do not incorporate all of the blocks shown in FIG. 2.

In one embodiment of the ear monitoring device 10, a source 50 generates and transmits a test signal into the patient's ear 15. The test signal enters the patient's ear 15 through the probe 20 positioned in the ear canal 25 as illustrated in FIG. 1. A signal generator 55 monitors the condition within the patient's ear 15 through the probe 20 positioned within the ear canal 25. One embodiment of the signal generator 55 is a transducer. The signal generator 55 converts the condition within the patient's ear 15 into an electrical signal which is presented to a filter 60. The filter 60 filters out any test signal from the electrical signal and presents the filtered signal to a compressor 65. The compressor 65 reduces the dynamic range of the filtered signal and presents the signal to the output 30. The output 30 makes the signal accessible to the audio transducer 35.

In one mode of operation of this embodiment of the ear monitoring device 10, the ear monitoring device administers test signals to the patient's ear 15. During the test, the source 50 presents a test signal to the patient's ear 15 though the probe 20 in the ear canal 25. Environmental noise may enter the ear canal 25 from the sides of the probe 20 if the probe 20 is not positioned properly in the ear canal 25. Biological noise may enter the ear canal 25 from the patient's activities such as teeth grinding, etc. In addition, the patient's ear 15 may emit signals in response to the test signal. Thus, the condition in the patient's ear 15 will comprise the test signal, may comprise noise, and may comprise emissions from the patient's ear 15. The condition of the patient's ear 15 is presented to the signal generator 55 through the probe 20 in the ear canal 25. The signal generator 55 converts the condition of the patient's ear 15 into an electrical signal. The electrical signal is filtered by the filter 60. The filter 60 filters out the test signal present in the electrical signal, thus resulting in a signal comprising any noise and emissions from the patient's ear 15. The compressor 65 compresses the filtered signal and presents the filtered signal to the output 30 which sends the signal to the audio transducer 35.

The compressor 65 reduces the dynamic range of the filtered signal so that the signal presented to the output 30 for delivery to the audio transducer 35 doesn't contain large fluctuations in amplitudes. Thus, for a given amplitude range of input voltages, the compressor 65 produces a smaller range of output voltages. Therefore, the volume range of the signals is reduced by amplifying weak signals and attenuating strong signals. For example, if some of the noise contained in the filtered signal has a high amplitude and some of the emissions from the patient's ear 15 have a low amplitude, then large fluctuations in amplitudes are heard by the operator listening to the output from the audio transducer 35. The listener may find these large fluctuations in sound irritating, so the compressor 65 is used to reduce these large fluctuations.

This mode of operation allows the operator to listen for extraneous noise during the test and to reduce the noise by repositioning the probe 20 in the ear canal 25. Also, the operator can listen for possible emissions from the patient's ear 15, thus enabling the operator to audibly determine the results of the test while the test is progressing.

In another mode of operation of this embodiment of the ear monitoring device 10, the operator places the probe 20 in the ear canal 25 and checks for proper positioning of the probe 20 before beginning the test. Thus, the source 50 is not yet generating a test signal. Without a test signal, the patient's ear 15 will not emit any signals. Thus, the condition inside the patient's ear 15 comprises any extraneous noise that may have entered the ear canal 25, either environmental or biological noise. This extraneous noise is converted into an electrical signal by the signal generator 55, passes through the filter 60, is compressed by the compressor 65, and output to the audio transducer 35.

This mode allows the operator to listen for extraneous noise before the test begins. After the operator positions the probe 20 in the ear canal 25, but before starting the test, the operator can check for proper positioning of the probe 20 in the ear canal 25 by listening for extraneous noise. If the operator hears extraneous noise before staring the test, the operator can reduce the environmental noise by repositioning the probe 20 in the ear canal 25. In addition, the operator can reduce the biological noise by requesting the patient to minimize his activities.

In another embodiment of the invention, the ear monitoring device 10 does not contain the filter 60. Thus, the electrical signal from the signal generator 55 is presented to the compressor 65 and subsequently to the output 30 and the audio transducer 35. Thus, the operator can listen to the test signal generated by the source 50 during the test since the test signal is not filtered out. If the test signal generated by the source 50 changes in a known way over the course of the test, the operator can audibly determine how the test is progressing. If no test signal is present because the test has not begun, then the operator can listen for extraneous noise as mentioned above.

In a further embodiment of the invention, the ear monitoring device 10 does not contain the compressor 65. Thus, the electrical signal from the signal generator 55 is presented to the filter 60 and subsequently to the output 30 and the audio transducer 35. Thus, if the test has begun, the operator can listen for any extraneous noise and any emissions from the patient's ear 15. If the test has not begun, the operator can listen for any extraneous noise. The operator will hear the full dynamic range of the extraneous noise and emissions from the patient's ear 15 because the signals were not compressed.

In still a further embodiment of the invention, the ear monitoring device 10 does not contain the filter 60 or the compressor 65. Thus, the electrical signal from the signal generator 55 is presented to the output 30 and the audio transducer 35. Thus, the operator can listen to the test signal generated by the source 50 during the test since the test signal was not filtered out. If the test signal generated by the source 50 changes in a known way over the course of the test, the operator can audibly determine how the test is progressing. If no test signal is present because the test has not begun, then the operator can listen for extraneous noise. The operator will hear the full dynamic range of the test signal and any extraneous noise because those signals were not compressed.

In any of the embodiments mentioned above, the source 50 and/or the audio transducer 35 may be external to the ear monitoring device 10.

Figure 3:
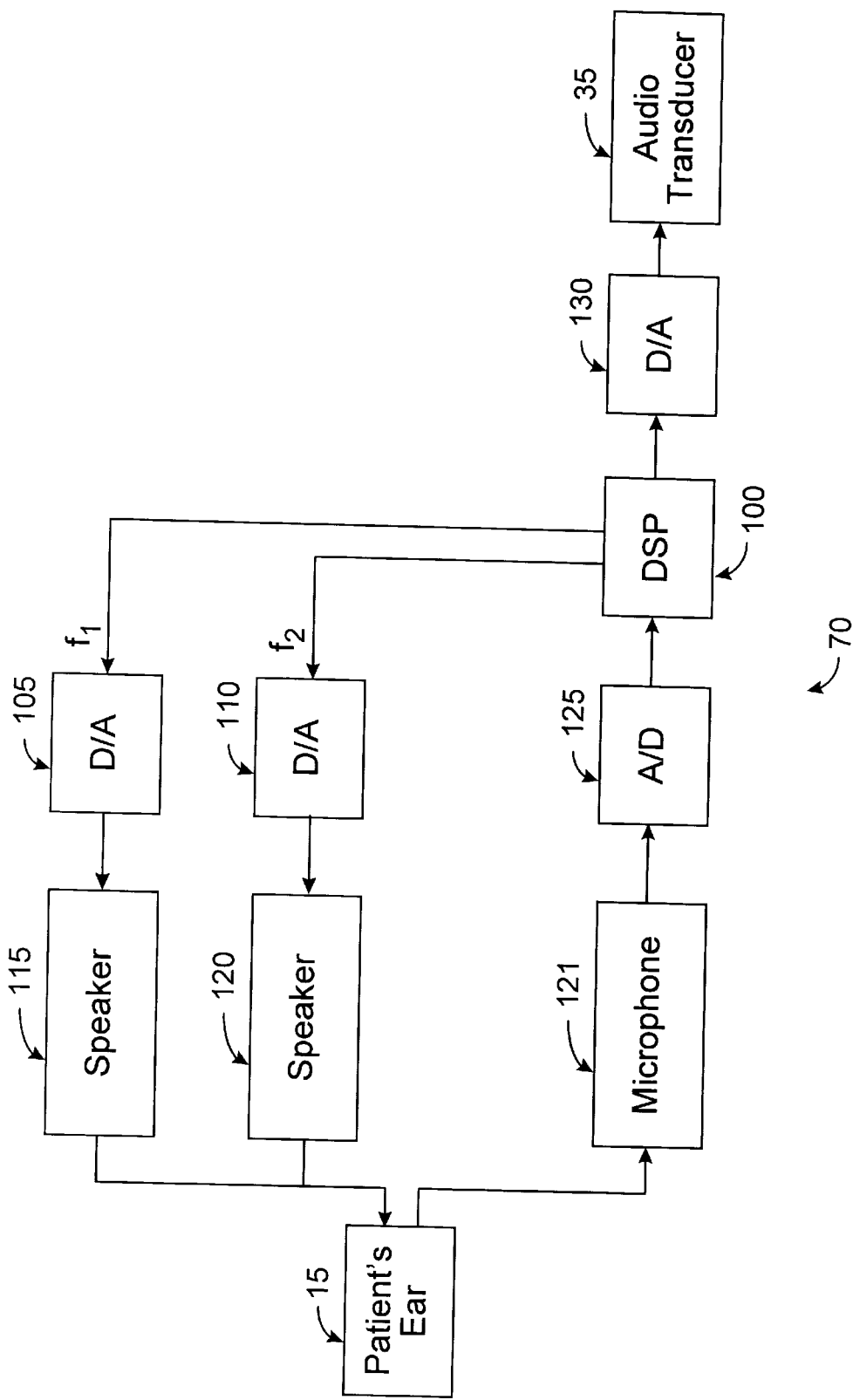
FIG. 3 is a block diagram of an ear monitoring device, according to the present invention, used in the realm of otoacoustic emissions testing.

FIG. 3 is a block diagram of an ear monitoring device, according to the present invention, used in the realm of otoacoustic emissions testing. An otoacoustic emissions tester 70 generates two tones in the audible range and transmits the tones into the patient's ear 15. If the patient's ear 15 is healthy, the patient's ear 15 emits a signal at frequencies which are a combination of the frequencies of the two tones. Thus, if two test signals are generated at frequencies $f_1$ and $f_2$, a healthy patient's ear 15 will emit a signal at frequencies which are a combination of $f_1$ and $f_2$. The strongest signal emitted from the patient's ear 15 occurs at the frequency of $(2*f_1)-f_2$. This is called the distortion product.

In addition, the otoacoustic emissions tester 70 generates two test signals with frequencies that change in a known fashion over the course of the test. Thus, a healthy patient's ear 15 will emit a distortion product with a frequency that changes over the course of the test.

In FIG. 3, an otoacoustic emissions tester 70 is a particular embodiment of the ear monitoring device 10 of FIG. 2. A digital signal processor (DSP) 100 performs the functions of the source 50 of FIG. 2. The DSP 100 generates two test signals at frequencies $f_1$ and $f_2$ respectively. The DSP 100 generates the two tones with a look-up table (LUT). The LUT contains one cycle of a sine wave. The LUT is stepped through at different rates to generate test signals at different frequencies. Because the DSP operates on digital signals, the two test signals must be converted to analog signals using the analog-to-digital converters 105 and 110. The analog test signals are converted to audible signals by the speakers 115 and 120. The audible signals enter the patient's ear 15 through the probe 20 positioned in the ear canal 25 as illustrated in FIG. 1.

The DSP 100 also performs the function of the filter 60 and the compressor 65 in FIG. 2.

The microphone 121 replaces the signal generator 55 in FIG. 2 since the otoacoustic emissions and the test signals in the ear canal 25 are sound waves. The microphone 121 monitors the condition within the patient's ear 15 through the probe 20 positioned within the ear canal 25. The microphone 121 converts the condition within the patient's ear 15 into an electrical signal. Again, because the DSP 100 operates on digital signals, the electrical signal from the microphone 121 must be converted to digital before being presented to the DSP 100. The analog-to-digital converter 125 performs this conversion. The DSP 100 receives the signal from the A/D 125 and performs any filtering and compressing as required by the mode of operation of the otoacoustic emissions tester 70. The otoacoustic emissions tester 70 has the same modes of operation as the ear monitoring device 10 discussed previously.

The DSP 100 presents the signal to a D/A 130 for conversion to an analog signal, and the analog signal is presented to the audio transducer 35.

In the otoacoustic emissions tester 70, the DSP 100 is a Motorola 56303 digital signal processor, the D/A's 105 and 110 and the A/D 125 are the Burr Brown 3001 Codec, and the D/A 130 is a Linear Technology LTC 1451 digital-to-analog converter. The microphone is a low noise microphone. The functions performed by these parts are not unique, and any comparable parts may be used.

The filtering performed by the DSP 100 is implemented with a fourth order IIR filter with zeros at the test signal frequencies and poles at the distortion product frequency.

The compression performed by the DSP 100 reduces the dynamic range of the signals by adjusting gain according to the level of the signal. This is implemented by detecting the peak value of the signal and using the peak value to address a LUT. The LUT contains the appropriate gain for that peak value. The software that implements the compression within the DSP 100 is contained in the appendix.

We claim:

1. A system that enables audible monitoring of a condition in an ear by a test operator during an ear test on a subject, said system comprising:
    a probe for inserting into an ear canal of a subject;
    at least one speaker for emitting a test signal into the ear via the probe;
    a signal generator for receiving from the ear via the probe an audio signal representative of a condition within the ear and for generating therefrom an electrical signal; and
    an audio transducer for converting the electrical signal into an audible signal.

2. The system of claim 1, wherein the signal generator comprises a transducer.

3. The system of claim 1, wherein the signal generator comprises a microphone.

4. The system of claim 3, further comprising a source for generating the test signal.

5. The system of claim 4, wherein the test signal comprises at least two audio frequencies.

6. The system of claim 5, further comprising:
    a filter for filtering out at least any of the test signal present in the electrical signal to prevent at least any of the test signal from being converted by the audio transducer.

7. The system of claim 5, further comprising:
    a compressor for reducing the dynamic range of the electrical signal.

8. The apparatus of claim 5, further comprising:
    a filter for filtering out at least any of the test signal present in the electrical signal to prevent at least any of the test signal from being converted by the audio transducer; and
    a compressor for reducing the dynamic range of the filtered electrical signal.

9. The system of claim 1, further comprising: a compressor for reducing the dynamic range of the electrical signal.

10. The system of claim 1, further comprising a source for generating the test signal.

11. The system of claim 10, further comprising:
    a filter for filtering out at least any of the test signal present in the electrical signal to prevent at least any of the test signal from being converted by the audio transducer.

12. The system of claim 10, further comprising:
    a compressor for reducing the dynamic range of the electrical signal.

13. The system of claim 10, further comprising:
    a filter for filtering out at least any of the test signal present in the electrical signal to prevent at least any of the test signal from being converted by the audio transducer; and a compressor for reducing the dynamic range of the filtered electrical signal.

14. A method of audibly monitoring a condition in an ear, the method comprising the steps of:

emitting, into a subject's ear, a test signal;

receiving, from the subject's ear, an audio signal representative of a condition within the ear;

generating from the audio signal a corresponding electrical signal; and transducing said electrical signal into an audible signal for monitoring by an operator.

15. The method of claim 14, further comprising the step, after the generating step, of reducing the dynamic range of the electrical signal.

16. The method of claim 14, further comprising the step, before the emitting step, of generating the test signal.

17. The method of claim 16, further comprising the step, after the step of generating from the audio signal a corresponding electrical signal, of filtering out at least any of the test signal present in the electrical signal to prevent at least any of the test signal from being transduced.

18. The method of claim 16, further comprising the step, after the step of generating from the audio signal a corresponding electrical signal, of reducing the dynamic range of the electrical signal.

19. The method of claim 16, further comprising the steps of:

after the step of generating from the audio signal a corresponding electrical signal, filtering out at least any of the test signal present in the electrical signal to prevent at least any of the test signal from being transduced; and after the filtering step, reducing the dynamic range of the filtered electrical signal.

20. An system that enables audible monitoring of a condition in an ear by a test operator during an ear test on a subject, said system comprising:

at least one speaker for emitting a test signal into an ear;

a signal generator for converting an audio signal received from the ear into an electrical signal; and an audio transducer for converting the electrical signal into an audible signal.

21. The apparatus of claim 20, wherein the audio transducer comprises an earphone.

* * * * *